United States Patent [19]

Pegel

[11] 4,198,401

[45] Apr. 15, 1980

[54] ACTIVE PLANT EXTRACTS OF HYPOXIDACEAE AND THEIR USE

[76] Inventor: Karl H. Pegel, King George V Ave., Durban Natal, South Africa

[21] Appl. No.: 16,387

[22] Filed: Mar. 1, 1979

Related U.S. Application Data

[62] Division of Ser. No. 856,507, Dec. 1, 1977, Pat. No. 4,160,860.

[30] Foreign Application Priority Data

Dec. 30, 1976 [DE] Fed. Rep. of Germany ....... 2659465

[51] Int. Cl.² .................... A61K 35/78; A61K 31/705
[52] U.S. Cl. ...................................... 424/195; 424/182
[58] Field of Search ..................... 424/195, 182; 536/5

[56] References Cited

U.S. PATENT DOCUMENTS 3,933,789  1/1976  Pegel ....................................... 536/5

FOREIGN PATENT DOCUMENTS

| 2015877 | 10/1970 | Fed. Rep. of Germany . |
| 2312285 | 9/1973 | Fed. Rep. of Germany . |
| 2251695 | 4/1974 | Fed. Rep. of Germany . |
| 7001861 | 3/1970 | South Africa . |
| 1259503 | 1/1972 | United Kingdom . |
| 1417272 | 12/1975 | United Kingdom . |

*Primary Examiner*—Donald B. Moyer
*Attorney, Agent, or Firm*—Cushman, Darby & Cushman

[57] ABSTRACT

Plant material derived from the family Hypoxidaceae is heated at a temperature of at least 60° C. for a sufficient period to ensure enzyme destruction and is then extracted at a temperature of 0°–30° C. with aqueous alcohol containing 30–75 volume percent ethanol for about 1 to 15 days to obtain a pharmaceutically active material.

13 Claims, No Drawings

ACTIVE PLANT EXTRACTS OF HYPOXIDACEAE AND THEIR USE

This is a division of application Ser. No. 856,507 filed Dec. 1, 1977, now U.S. Pat. No. 4,160,860.

BACKGROUND OF THE INVENTION

The invention is directed to active materials extracted from plants of the family Hypoxidaceae.

The plant family of Hypoxidaceae belongs to the monocotyledons and includes relatively few genera which, however, occur world wide except for most parts of Europe and northern Asia. Member genera of the Hypoxidaceae family are, for example, Curculigo, Empodium, Hypoxis, Spiloxene, Rhodohypoxis, Campynema, Campynemanthe, Pauridia and Xiphidium.

Until now relatively little has been published about this plant family and its components. In these publications it has been shown that the members of this family predominantly contain various sugars and sugar derivatives such as mucilage hemicellulose, polysaccharides and specific sugars such as xylose, glucose, mannose, fructose, sucrose and glucuronic acid. Phenolic compounds have also been detected such as for example coumaric acid, caffeic acid, ferulic acid and ellagic acid as well as quercetin. Furthermore, there are indications of the presence of anthocyanidines; it has also been asserted that chelidonic acid is present, although there are doubts about this. In this plant family alkaloids or saponins, have not been found, but there have been numerous references to the occurrence of sterols, sterol glycosides, and steroid glycosides.

Until now there have been no authenticated reports that toxic compounds are present in the plants. It appears on the contrary that some species have been used in the folk medicine of different countries and even as a food, although generally only in times of famine and other emergencies.

Only in recent times has reference been made to the fact that members of the Hypoxidaceae family have surprising medicinal properties. For example, the production of extracts of the Hypoxis genus is described in the German OS 20 15 877 corresponding to the British Pat. No. 1,259,503, the German OS 22 51 695 and the German OS 23 12 285 corresponding to the British Pat. No. 1,417,272 and the U.S. Pat. No. 3,933,789. In these publications reference has been made to the fact that the activity of the extracts depends on sterol glycosides or steroid glycosides in them and that these extracts show activity especially in the treatment of benign prostate hypertrophy and its attendant phenomena.

With respect to the production of extracts from Hypoxis species the German OS 20 15 877 refers only to the extraction of comminuted fresh or previously dried tubers or corms with water, ethanol or aqueous ethanol. In contrast the German OS 22 51 695 specifies that the corms of the Hypoxis species used have to be dried at temperatures not exceeding 40° C. before they are extracted. According to this publication the extraction can also be carried out with, amongst others, a mixture of water and lower alcohols.

On the other hand the German OS 23 12 295 refers in detail to the absolute necessity that sterolin degrading enzymes in the corms have to be destroyed by heating them to at least 60° C. before carrying out the actual extraction. In addition it is shown that especially sterolin rich extracts can only be obtained if the extraction is carried out by boiling the plant material in water. In contrast the extraction with 60% ethanol yields an extract which contains only traces of sterolins and sterolin compounds.

SUMMARY OF THE INVENTION

Surprisingly it has now been found that medicinally particularly effective extracts of plants of the family Hypoxidaceae can be produced if the fresh plant material, either whole or immediately after comminution is heated to a temperature of at least 60° C. or more and is subsequently extracted over a period of several hours up to 15 days at temperatures between 0° C. and the boiling point with a mixture of water and ethanol having an alcohol content of 30–75 volume percent and preferably an alcohol content of 60 volume percent.

The fact that the extracts produced in this fashion show an extraordinarily good effect in the treatment of various diseases is surprising since these extracts contain substantially less sterolins than those produced according to German OS 23 12 285. It therefore becomes apparent that besides sterolins and sterolin derivatives, other not yet identified compounds are extracted by means of the described procedure and that these compounds either such or in synergistic action with the sterolins show a definite activity. But, also on comparison with the procedure detailed in the German OS 22 51 695 the activity of the extracts produced by the invention was surprising since according to the invention it is absolutely necessary that before the corms are extracted they are heated to temperatures of at least 60° C., while the process described in the mentioned German OS 22 51 695 requires that the plant parts are dried at temperatures of not over 40° C. or alternatively they are worked up fresh.

According to the invention the extracts are produced in such manner that freshly harvested plant material, that is particularly tubers or corms of plant species of the family Hypoxidaceae, as a whole or comminuted or cut is heated as soon as possible to temperatures of at least 60° C. and preferably 80°–100° C. For example, heating can be carried out as a treatment with steam, boiling water or in a pasteurization process. The duration of this heat treatment depends on the particular plant material, the thickness thereof and the medium used. It is necessary that the entire plant material be thoroughly heated to temperatures of above 60° C. so that the degrading enzymes are destroyed completely. Subsequently the plant material is comminuted if this has not been done earlier and is extracted with aqueous ethanol containing 30–75 and preferably 60 volume percent of alcohol at temperatures of 0° C. to the boiling point and preferably 0°–30° C. for about 1–15 days. The required time depends on the temperature and the amount of extraction agent, thus at a temperature of 25° C. the extraction can be ended in 7 days. The extraction is preferably carried out at room temperature since at higher temperatures of 40° C. and more too many inactive ballast substances such as sugars and tannins are co-extracted.

The various already mentioned genera of the Hypoxidaceae can be used as extraction material as long as they contain sterolin compounds. It has been established that if sterolins are present then the other aqueous alcohol extractable, but not yet identified compounds are present as accompanying products. Preferably as extraction material plants are used which occur in sufficient amounts to make an industrial process viable.

Amongst these are especially the species of the Hypoxis and Curculigo genera.

The extract produced according to the invention can be used as such if for example in specific cases an enrichment in foodstuff is carried out if it is intended to provide a maintenance dosage for treating specific diseases. Preferably however, the extract obtained is concentrated in a vacuum and subsequently spray dried. The so obtained powder can then be incorporated into pharmaceutical products by well established methods.

Clinical investigations of the so obtained extract have shown that in the treatment of most diseases doses of about 50–1000 mg of the extract per day produce an excellent effect. Usually doses of 50–200 mg are given several times a day and preferably a dose of 100 mg 3 times daily. Also from this it can be seen that the sterol- or steroid glycosides cannot be the only active material. It was already established in the German OS 23 12 285 that in the extraction of fresh Hypoxis corms with 60% ethanol at refrigeration temperatures over a period of 3 days a substantially reduced sterol glycoside content was detected. The reported value amounted to 0.23 mg sterol glycoside per 100 grams of extract while in the aqueous extraction for example 5.75 mg per 100 grams of extract or in extraction of the heat pretreated Hypoxis corms with boiling water a yield of 9.01 mg of sterol glycoside per 100 grams of extract was obtained. In my co-pendng filed application Ser. No. 843,496, filed Oct. 19, 1977 entitled "Sterolins and Their Use" and corresponding to the German P 26 59 466 there is described in addition that the preferred effective dosage for sterol glycosides is about 0.45 mg per day. This dosage is clearly higher than the preferred doses of the extracts which have a relatively small sterol content.

In the pharmacological investigation of the extracts produced by the invention it was found that both in the examination of the acute and the chronic toxicity no toxic phenomena or organ changes could be detected. Also, in the clinical examination of the extract no undesired side effects were noted. On the contrary, the extract of the invention distinguishes itself by its good tolerance and high effectivity.

In the clinical investigations it has been shown that the extracts produced according to the invention have a beneficial prophylactic and/or curative effect on a large number of disease conditions. According to knowledge gained so far this applies to the following diseases:

(A) Diseases of the Gastro Intestinal Tract and Metabolic Disturbances (1) Ulcers.

(B) Physiological deviations in the Urogenital Tract (1) Benign prostate hypertrophy and complications arising from it; and, (2) Diseases of the urinary tract.

(C) Diseases of the Blood and Blood Forming Organs (1) Hyperlipidemia and its retrogressive manifestations.

(D) Diseases of the Cardiovascular System (1) Edematous conditions; and, (2) Prophylactic and curative agents against vascular diseases including varicose veins and hemorrhoids.

(E) Dermatological Diseases (1) Dermatitis including eczema, acne and similar conditions.

(F) Diseases of the Skeletal System and Muscles (1) Inflammations; and, (2) Arthritic and Rheumatic Diseases; and (3) Increased uric acid level.

The process can comprise, consist essentially or consist of the steps employed and the materials can comprise, consist essentially of or consist of those set forth.

The invention will be further explained in the following examples.

DESCRIPTION OF THE PREFERRED EMBODIMENTS

EXAMPLE 1

Production of the Extract 6 kilogram of fresh washed corms of *Hypoxis rooperi* were treated for 20 minutes at 120° C. with super-heated steam and then cut directly into 12 liter of 60% aqueous ethanol. This mixture was allowed to stand for 7 days at 28° C. and stirred twice daily for about 5 minutes. 12 liter of an extract are obtained, preferably by means of filtration.

(a) Six liter of this extract yielded after spray drying, 180 gram of a powder which corresponds to a 6% yield. This powder contained per 100 gram 2.5 mg of sterolins calculated as sitosteryl $\beta$-D-glucoside. The so obtained dried extract can be incorporated according to Examples 2 and 3 into capsules, tablets, dragées, ointments and creams.

(b) Six liters were diluted with a further 3 liter of 60% ethanol to a solids content of 4%. The adjusted extract was bottled and each bottle provided with the instructions to use one teaspoon full of the contents as a single dose. A teaspoon contains on an average 2.5 ml of liquid; this corresponds in the present case to a content of 100 mg Hypoxis extract with 0.0025 mg of sterolins.

EXAMPLE 2

The Hypoxis extracts produced according to the process described in Example 1(a) can be incorporated by known methods into capsules, tablets and dragées.

(a) Production of Capsules

The content of extract in a single dose is preferably 100 mg and usually together with up to 100 mg of lactose or glucose as carrier and 1 to 2 mg Aerosil ®(pyrogenic silica) or magnesium sterate as disintegrating agent or lubricant. The final extract, mixed with the additives is filled into plug capsules.

(b) Production of Tablets 800 gram of Hypoxis extract, 752 gram of lactose with a preferred particle size of not over 0.15 mm and 1400 gram of potato starch were intimately mixed. This mixture was granulated with a solution of 243.2 gram of gelatin and 4.8 gram of glycerine and 2500 ml of water and the granulate was dried under reduced pressure at room temperature. The granulate was then worked to about 8000 tablets with a tablet weight of 400 mg. Each tablet contained accordingly 100 mg of Hypoxis extract, 94 mg of lactose, 175 mg of potato starch, 30.4 mg of glycerine and 0.6 mg of glycerine.

(c) Production of Dragées 420 gram of Hypoxis extract, 2310 gram of lactose and 420 gram of sucrose, both having a preferred particle size of not over 0.15 mm were intimately mixed. This mixture was granulated with a solution of 63 gram of gelatin in 2.1 liter of water. The granulate formed was dried under reduced pressure at 45° C. and intimately mixed with 16.8 gram of magnesium stearate. This mixture (3125 gram) was moulded to about 4000 kernels which were subsequently coated with, a suitably coloured dragée coating. Each dragée contained 100 mg Hypoxis extract, 550 mg lactose, 100 mg sucrose, 15 mg gelatin and 4 mg magnesium stearate.

EXAMPLE 3

(a) Production of an ointment Containing Hypoxis Extract

A melted mixture of 90 gram of emulsifying cetylstearyl alcohol, 100 gram of viscous liquid paraffin and 100 gram of white Vaseline (petroleum jelly) were heated to 60° C. and treated with similarly warmed solution of 30 gram Hypoxis extract prepared according to Example 1a in 680 gram of water. The mixture was stirred until it had reached ambient temperature and yielded an ointment containing 3% of Hypoxis extract.

(b) Production of a Cream Containing Hypoxis Extract 500 gram of wool wax alcohol were warmed to 50° C. and treated in small amounts with a equally warmed solution of 30 gram of Hypoxis extract prepared according to Example 1(a) in 470 gram of water. The cream was stirred until it had reached ambient temperature, whereupon the vaporised portion of water was replenished. The cream contained 3% of Hypoxis extract.

EXAMPLE 4

Pharmacological Test of the Anti-inflammatory Effect of the Extract Produced According to Example 1

Oral Feeding 24 male rats of the Sprague-Dawley stock with an average weight of 230 gram were accustomed to the test conditions. The liquid extract was then given in 3 equal doses 48, 24 and 1 hour before administering the inflammation causing agent. Doses of 1 ml or 2 ml of the extract per 100 gram of body weight were administered by force feeding. The inflammation causing agent, namely, fresh chicken egg white, was homogenised in 0.9% NaCl solution to a concentration of 12.5 volume % and 0.1 ml of the resulting solution was injected into the plantar area of the right hind paw.

Half of the test amimals were killed after 5 hours to determine the acute inflammation; the rest after 24 hours to determine the residual inflammatory action. The resulting edema were compared by weight with the left hind paw into which a similar volume of the saline solution only had been injected as a control. The average change in weight of the group was compared with a control group which in place of the test compound had only received water in an amount of 1.0 ml per 100 gram of body weight.

The average reduction of the inflammatory reaction is seen from the following table wherein the formation of edema in the animals of the control group was established as 100%.

| I. Reduction of the Acute Inflammatory Response 5 Hours After Administration of Inflammatory Agent | |
|---|---|
| 1 ml/100 gram | 2 ml/100 gram |
| 11% | 17% |

| II. Reduction of the Residual Inflammatory Response 24 Hours After Administration of Inflammatory Agent | |
|---|---|
| 1 ml/100 gram | 2 ml/100 gram |
| 31,7% | 33,6% |

EXAMPLE 5

Chronic Toxicity Study

The investigation of the chronic toxicity was carried out with young male rats of the Sprague-Dawley stock having an average initial weight of about 175 gram. The control group and the treated groups have always consisted of 12 animals. The control group received pure water while the test groups were given water containing liquid extract prepared according to Example 1, that is, one test group received a supplement of 25%, another a supplement of 50% and a last group a supplement of 100% of extract, thus in effect the extract of the invention in place of pure water.

The study was carried out with all groups for 49 days. After ending the test it was established that with the exception of the test group which contained 100% extract and in which one animal died of unknown causes, all animals showed a normal increase in weight and no macro- or microscopic pathological changes were observed.

The summarized results are exhibited in the following table:

|  | Control Group | 25% Supplement | 50% Supplement | 100% Supplement |
|---|---|---|---|---|
| Average body weight after 49 days | 326 g | 327 g | 313 g | 321 g |
| Initial body weight | 177 g | 174 g | 177 g | 175 g |
| Average gain in weight | 149 g | 153 g | 136 g | 146 g |
|  |  |  |  | 1 died |
| Total intake in liquid/kg | 4966 ml | 5541 ml | 5185 ml | 4464 ml |
| Average daily intake of liquid/kg | 101 ml | 113 ml | 106 ml | 91 ml |
| Conversion value of the daily intake for a person weighing 50 kg | 5050 ml | 5650 ml | 5300 ml | 4550 ml |
| Conversion value for a person weighing 50 kg based on the 49 days total |  |  |  |  |

|  | Control Group | 25% Supplement | 50% Supplement | 100% Supplement |
|---|---|---|---|---|
| intake | 247.45 l | 276.45 l | 259.7 l | 222.95 l | g = gram
l = litre
ml = millilitre

EXAMPLE 6

Clinical Testing

In the clinical trials liquid extracts according to Example 1(b) were used and capsules according to Example 1(a) and Example 2.

In all 1198 patients between the ages of 52 and 89 years were treated with these preparations. The average age of the patients was 69 years.

The patients received 30 drops 3 times a day, that is, after meals. The capsules were also dispensed 3 times daily after meals. These dosages were found to be particularly favourable although in several cases higher doses were also dispensed. The preparations were prescribed for some patients in combination with antibiotics, sulfonamides, furantoins, cardiac and circulatory agents; even with the combined administration of these agents an excellent tolerance was established.

The duration of the treatment generally extended over several months, in several cases a long-term treatment of over 1½ years was carried out. Already after 14 days the patients consistently showed a distinct subjective relief.

The following could be established objectively:

(a) Residual Amounts of Urine (1) Residual amounts of urine of up to 100 ml regressed completely in 100% of the cases.

(2) Residual amounts of urine between 100 and 200 ml regressed in about 90% of the cases.

(3) Residual amounts of urine between 200 and 500 ml regressed in 72% of the group. 10% of these patients retained residual amounts of urine of 100 ml, the remainder had to be operated or had to be electroresectioned.

(b) Size of the Prostate

In 1150 cases the size of the gland had decreased distinctly by using the rectal touch test as a criterion.

In only 4% of the investigated cases were no changes observed when measuring the colliculus interval. On average an interval reduction of 0.6 to 0.8 cm was achieved. In many cases the interval was reduced from 4.2 to 3.2 cm, in several patients from 3.2 to 2.4 cm and in others from 3.0 to 2.0 cm.

(c) Bladder Pressures

In 88% of the manometrically investigated patients an increase of the micturition pressure resulted under the influence of the preparations. Low initial values of 40 to 60 mm Hg increased after a treatment period of 3 months to 80 to 100 mm Hg. As a rule the resistance pressure was lowered by 10 to 20 mm Hg. In 12% of the investigated patients no change of the bladder pressure could be observed while under the medication. But the measurements showed that no further deterioration took place.

(d) Urine Findings

It is understood that an improvement of the urine condition is reflected by a decline of the number of leucocytes in the sediment, that is huge to large amounts of leucocytes before treatment, while at the end of the treatment only isolated leucocytes are detectable.

A decline of the number of leucocytes was obtained in 96% of all of the cases.

In those cases in which the urinary tract infection was produced by Coli or Proteus bacteria the cultures of 863 patients (72% of all cases) were sterile at the end of the treatment period. In 156 patients (about 13%) this outstanding result was not produced but a clear improvement of the bacteriological condition was obtained, i.e. only isolated germs were still detectable after the treatment. The remainder of the infections were caused by Pyocyaneus infections and they could not be influenced by medication.

No deterioration in any of the examined parameters (sediments, bacteriological) was observed even after prolonged treatment.

(e) X-ray Controls

Because of the inability to empty the bladder by reason of the enlarged prostate at the neck of the bladder in the patients residual urine collection usually occurs and results in a urine build up in the upper urinary tract, and thus give rise to a well-defined dilation of the ureters, the renal pelvis and the cups. This can be observed by means of X-rays, through a separating urograph or an infusion urograph. Theoretically these obstructions retrogress once the obstacle at the neck of the bladder has retrogressed. In many cases the retrogression can also be clearly established on suitable X-ray pictures. In 72 patients the interpretation of the X-ray pictures showed that obstructions formed in the upper urinary tract due to the prevention of discharge at the neck of the bladder through the enlarged prostate had plainly retrogressed. In several cases a clear retrogression was recognized within 4 to 6 weeks. In the majority of the cases a three-month treatment was necessary to detect a distinct retrogression of the obstruction by X-ray examination.

In none of the cases investigated and controlled by X-ray was there an enlargement of the upper urinary tract when they were treated with the preparations.

EXAMPLE 7

Clinical Trials of the Effect in Rheumatic Arthritic Conditions

Patients with chronic polyarthritis, Morbus Reiter and various diseases of the rheumatic cycle were treated with 3 capsules according to Example 1(a) and Example 2.

With these a distinct retrogression of inflammation could be observed. Because of the subjective freedom from pain and the objective detection of reduction of the inflammatory symptoms even with patients who had received anti-corticosteroid hormones for years the administration of cortisones could be stopped. Likewise the administration of so-called symptomatic antirheumatics could be stopped in most cases.

EXAMPLE 8

Patients with various manifestations of chronic gout were treated daily over a period of 6 months with 3 capsules according to Example 1(a) and Example 2. The capsules were given before each main meal. Already after the first month of treatment none of the patients suffered a further gout attack.

What we claim is:

1. A process of combatting a human illness selected from the group consisting of inflammatory illness, gout and benign hypertrophy comprising administering to a patient suffering therefrom an effective amount of an extract of plant material of the family Hypoxidaceae prepared by a process comprising the steps of heating the plant material to at least 60° C. to deactivate the steroline specific degrative enzymes and thereafter extracting at 0° to 30° C. with aqueous alcohol containing 30–75 volume percent ethanol for 1–15 days.

2. A process according to claim 1 wherein the effective amount is between 50 and 1000 mg a day.

3. A process according to claim 2 wherein the dosage is 300 mg a day.

4. A process according to claim 1 wherein the plant is *Hypoxis rooperi*.

5. A process according to claim 1 wherein the illness is an inflammatory illness.

6. A process according to claim 5 wherein the illness is arthritis.

7. A process according to claim 5 wherein the illness is a rheumatic illness.

8. A process according to claim 5 wherein the illness includes edema.

9. A process according to claim 5 wherein the plant is *Hypoxis rooperi*.

10. A process according to claim 1 wherein the illness is benigh prostate hypertrophy.

11. A process according to claim 10 wherein the plant is *Hypoxis rooperi*.

12. A pharmaceutical product comprising an extract of plant material of the family Hypoxidaceae prepared by a process comprising the steps of heating the plant material to at least 60° C. to deactivate the steroline specific degrative enzymes and thereafter extracting at 0° to 30° C. with aqueous alcohol containing 30–75 volume percent ethanol for 1–15 days together with a pharmaceutically acceptable carrier.

13. A pharmaceutical product according to claim 12 wherein the plant material is *Hypoxis rooperi*.